United States Patent [19]

Nudelman

[11] 3,971,779

[45] July 27, 1976

[54] 7-[2-(5-AMINO-1,3,4-THIADIAZOL-2-YLTHIO)ACETAMIDO]CEPHALOSPORINS

[75] Inventor: Abraham Nudelman, Bala Cynwyd, Pa.

[73] Assignee: American Home Products Corporation, New York, N.Y.

[22] Filed: Feb. 7, 1975

[21] Appl. No.: 547,832

[52] U.S. Cl. .............................. 260/243 C; 424/246
[51] Int. Cl.² ....................................... C07D 501/34
[58] Field of Search ................................ 260/243 C

[56]  References Cited
UNITED STATES PATENTS
3,365,449   1/1968   Takano et al. .................. 260/243 C

OTHER PUBLICATIONS

Chow et al., Chemical Abstracts, vol. 78, 97, 680t (1973).

Kariyone et al., Chemical Abstracts, vol. 79, 92, 244q (1973).

*Primary Examiner*—Nicholas S. Rizzo
*Assistant Examiner*—Diana G. Rivers
*Attorney, Agent, or Firm*—Richard K. Jackson

[57]  ABSTRACT

7-[2-(5-Amino-1,3,4-thiadiazol-2-ylthio)acetamido]-cephalosporins having antibacterial activity are disclosed.

3 Claims, 1 Drawing Figure

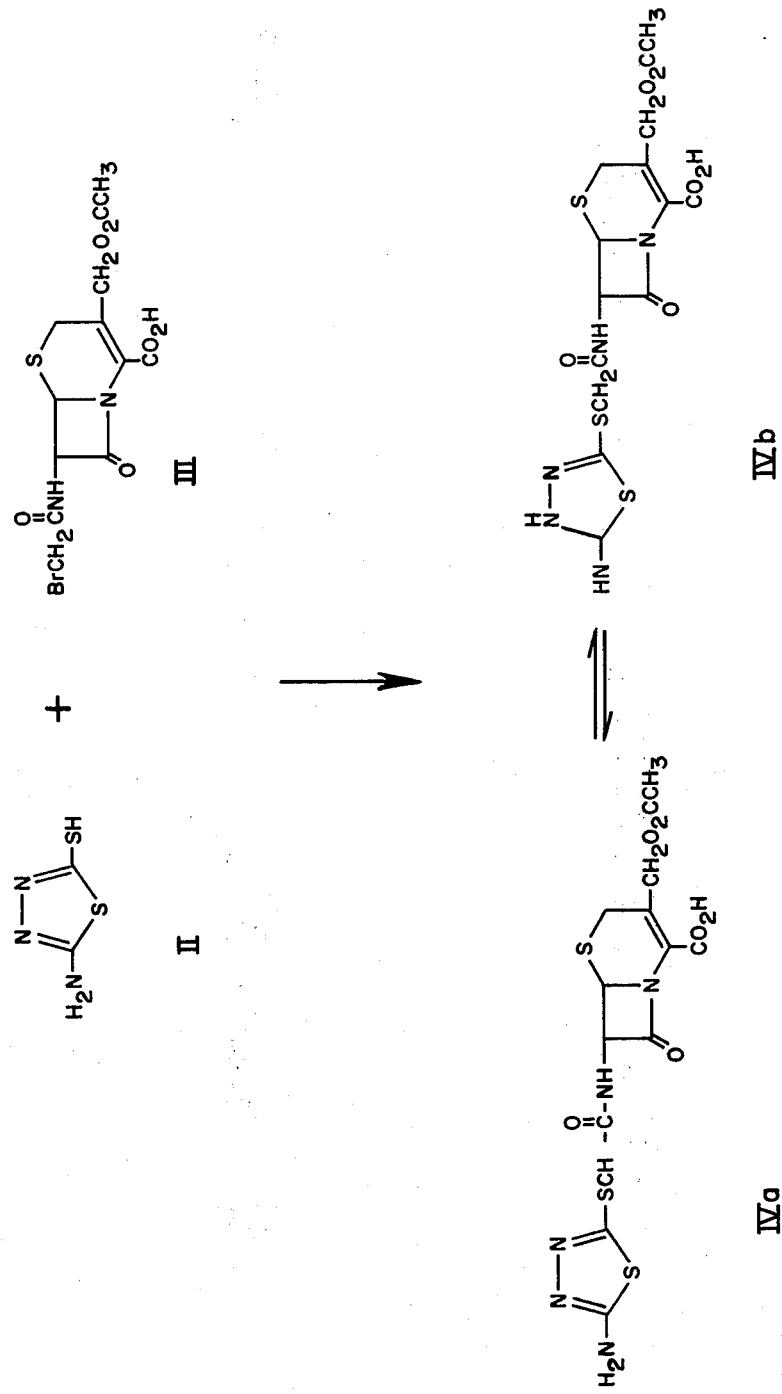

7-[2-(5-AMINO-1,3,4-THIADIAZOL-2-YLTHIO)ACETAMIDO]CEPHALOSPORINS

BACKGROUND OF THE INVENTION

U.S. Pat. No. 3,365,449 discloses and claims, inter alia, 7-[2-(5-lower alkanoyl amino-1,3,4-thiadiazol-2-ylthio)acetamido]cephalosporins. The present invention provides an unsubstituted amino group at the five position of the thiadiazole ring.

SUMMARY OF THE INVENTION

The invention sought to be patented in its principal composition aspect resides in the concept of a chemical compound having the formula:

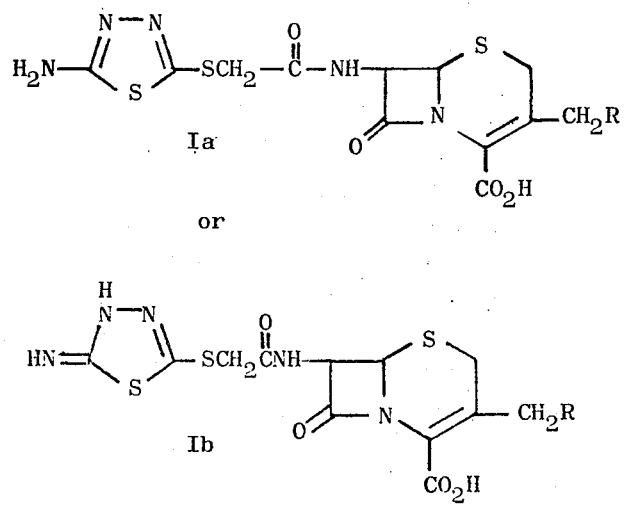

wherein R is hydrogen, acetoxy, or 2-(5-methyl-1,3,4-thiadiazolylthio); and the pharmaceutically acceptable addition salts thereof.

The tangible embodiments of this invention possess the inherent physical properties of being solids, of being substantially insoluble in water, and such solvents as acetone.

Examination of the compounds produced by the hereinafter described process reveals, upon infrared and nuclear magnetic resonance spectrographic analysis, spectral data supporting the molecular structure herein set forth.

The aforementioned physical characteristics, taken together with the nature of the starting materials, the mode of synthesis, and the elemental analysis confirm the structures of the compositions sought to be patented.

The tangible embodiments of the invention possess the inherent applied use characteristic of inhibiting the growth of gram-positive and gram-negative bacteria in vitro and gram-positive bacteria in vivo.

DESCRIPTION OF THE PREFERRED EMBODIMENT

In describing the process for the preparation of a specific embodiment of the invention, reference will be made to the FIGURE wherein the compounds are assigned Roman numerals for identification schematically, and wherein is illustrated schematically the reaction sequence for the preparation of a specific embodiment of Formula I, namely 7-[2-(4,5-dihydro-5-imino-1,3,4-thiadiazol-2-ylthio)acetamido]cephalosporanic acid (IV).

7-(2-Bromoacetamido)cephalosporanic acid (III) is treated with 5-amino-1,3,4-thiadiazole-2-thiol (II) in a solvent which will dissolve the reactants and in which the product is sparingly soluble, conveniently acetone, at moderate temperature, conveniently room temperature for a period of time sufficient to allow the reaction to take place to the desired extent, conveniently 5 days.

The product is then recovered by standard techniques. Separation by filtration and washing with fresh solvent is a convenient method.

While the process of the invention has been described with reference to the drawing which illustrates its application using 7-(2-bromoacetamido)cephalosporanic acid (III) as a starting material, it will be obvious to one skilled in the art that the process will be similarly applicable to the use of 7-(2-bromoacetamido)-3-methyl-8-oxo-5-thia-1-azabicyclo[4.2.0]oct-2-ene-2-carboxylic acid (V) and 7-(2-bromoacetamido)-3-[2-(5-methyl-1,3,4-thiadiazolylthio)methyl]-8-oxo-5-thia-1-azabicyclo[4.2.0]oct-2-ene-2-carboxylic acid (VI) as starting materials for the preparation of the other embodiments of Formula I contemplated with the scope of the invention.

The starting materials for the start of the invention are well-known and are readily obtained. 5-Amino-1,3,4thiadiazole-2-thiol (II) is commercially available. Compounds III, V, and VI may be prepared according to the method of U.S. Pat. No. 3,499,893 from the corresponding 7-amino compound.

The inhibition of the growth of bacteria (antibiotic) activity can be elicited by pharmacological evaluation procedures well-known in the art. Using the well-known agar serial dilution technique the compositions of the invention when tested are effective against gram-positive and gram-negative test organisms including penicillin resistant staphylococcus at an inhibitory concentration at or below 250 micrograms per milliliter.

When tested in vivo the compounds of the invention exhibit activity against gram-positive test organisms when administered orally to warm-blooded animals. Specific examples of such standard tests and the results are given in the examples infra.

In practicing the method of the invention the instant compositions may be administered in a variety of dosage forms either alone or in combination with pharmacologically acceptable carriers. They may be administered either orally or parenterally. The daily dose requirements will vary with the mode and frequency of administration, the size and species of the animal being treated and the severity and type of infection being treated.

One skilled in the art will recognize that the compounds of Formula I will exist in a tautomeric equilibrium which will consist of a mixture of the forma illustrated as Ia and Ib.

The term "pharmaceutically acceptable addition salts" includes in addition to addition salts of pharmacologically-acceptable organic and inorganic acids such as hydrochloric, hydrobromic, sulfuric, nitric, phosphoric, methane sulfonic, benzene sulfonic, and the like; alkali metal carboxylates and carboxylates of a pharmacologically-acceptable cation derived from ammonia or a basic amine.

The alkali metal carboxylates of the invention can be prepared by mixing stoichiometrically equivalent amounts of the free acids, preferably in aqueous solution, with solutions of alkali metal bases, such as sodium, potassium, and lithium hydroxides or carbonates, and the like, then freeze drying the mixture to leave the product as a residue. The amine salts can be prepared by mixing the free acids, preferably in solution, with a solution of the appropriate amine, in water, isopropanol, or the like, and drying the mixture to leave the product as a residue.

A "pharmacologically-acceptable cation derived from ammonia or a basic amine" contemplates the positively charged ammonium ion and analogous ions derived from organic nitrogenous bases strong enough to form such cations. Bases useful for the purpose of forming pharmacologically-acceptable non-toxic addition salts of such compounds containing free carboxyl groups form a class whose limits are readily understood by those skilled in the art. Merely for illustration, they can be said to comprise, in cationic form, those of the formula:

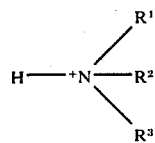

wherein $R^1$, $R^2$, and $R^3$, independently, are hydrogen, alkyl of from about 1 to about 6 carbon atoms, cycloalkyl of from about 3 to about 6 carbon atoms, monocarbocyclicaryl of about 6 carbon atoms, monocarbocyclicarylalkyl of from about 7 to about 11 carbon atoms, hydroxyalkyl of from about 1 to about 3 carbon atoms, or monocarbocyclicarylhydroxyalkyl of from about 7 to about 15 carbon atoms, or when taken together with the nitrogen atom to which they are attached, any two of $R^1$, $R^2$, and $R^3$ form part of a 5 to 6-membered heterocyclic ring containing carbon, hydrogen, oxygen, or nitrogen, said heterocyclic rings and said monocarbocyclicaryl groups being unsubstituted or mono- or dialkyl substituted, said alkyl groups containing from about 1 to about 6 carbon atoms. Illustrative thereof of R groups comprising pharmacologically-acceptable cations derived from ammonia or a basic amine are ammonium, mono-, di-, and trimethylammonium, mono-, di-, and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di-, and triethanolammonium, ethyl diethanolammonium, n-butylmonoethanolammonium, tris(hydroxymethyl)methylammonium, phenylmonoethanolammonium, and the like.

The term "pharmacologically acceptable carrier" contemplates usual and customary substances employed to formulate solid, oral unit dosages for pharmacological purposes, including in its broadest form animal feedstuff. It also includes those employed to formulate either in unit dose or multi dose form, oral and injectable suspensions and solutions, either directly or for reconstitution before administration.

The following examples further illustrate the best mode contemplated by the inventor for the practice of his invention.

EXAMPLE 1

7-[2-(4,5-Dihydro-5-Imino-1,3,4-Thiadiazol-2-ylthio)Acetamido]Cephalosporanic Acid To a solution of 7-(2-bromoacetamido)cephalosporanic acid (1.57 g., 0.04 moles) in 200 ml. of acetone is added 5-amino-1,3,4-thiadiazole-2-thiol (0.404 g., 0.04 moles). The precipitate formed after five days of stirring at room temperature is filtered, washed with acetone and dried to give 0.935 g. (42% yield) of the title compound as its hydrobromic acid addition salt. NMR Analysis: Signals at $\delta$=1.08 (singlet, 3 protons); 3.6 (broad singlet, 2 protons); 3.97 (singlet, 2 protons); 4.88 (quartet, 2 protons); 5.15 (doublet, 1 proton); 5.72 (doublet, 2 protons) ppm. in DMSO-$D_6$.

Analysis for: $C_{14}H_{16}BrN_5O_6S_3 \cdot 1.5H_2O$ Calculated:C, 30.30; H, 3.33; N, 12.86; Br, 14.43 Found:C, 30.26; H, 3.18; N, 12.39; Br, 14.51.

EXAMPLE 2

A stock solution of 7-[2-(4,5-dihydro-5-imino-1,3,4-thiadiazol-2-ylthio)acetamido]cephalosporanic acid as the hydrobromic acid addition salt containing 2,500 μg. of the active moiety is prepared in phosphate buffer. Two fold serial dilutions are prepared with phosphate buffer. One milliliter (ml.) quantities of each dilution are incorporated in 9 ml. seen agar in sterile Petri plates. The hardened surface is innoculated with test organisms using a Steers replicating device. The plates are incubated at 35° C. for 18 hours.

The test organisms are Bacillus subtilis (BA SU) 6633; Staphylococcus aureus (ST AU) 6538P, Smith CHP, and 3-180; Mycobacterium smegmatis (MY SM) 10143; Neisseria catarrhalis (NE CA) 8193; Pseudonomas aeruginosa (PS AE) 10145; Escherichia coli (ES CO) 9637, and 920; Escherichia intermedia (ES IN) 65-1; Salmonella paratyphi (SA PA) 11737; Enterobacter aerogenes (EN AE) 13048; Klebsiella pneumoniae (KL PN) 10031; Bordetella bronchiseptica (BO BR) 4617; Proteus vulgaris (PR VU) 6896; and Herellea species (HE SP) 9955. These organisms are grown for 18 hours in Brain heart infusion at 35° C. Prior to use the cultures are diluted 10 fold with the infusion, except in the case of Mycobacterium. The latter is grown in Emerson's broth for 5 days at 28° C. in shaker flasks and used undiluted.

The minimum concentrations (MIC) required to completely inhibit the growth of each organism is as follows:

| Organism | MIC (μg/ml.) |
|---|---|
| BA SU 6633 | .122 |
| ST AU 6538P | .488 |
| ST AU SMITH | .244 |
| ST AU CHP | .976 |
| ST AU 3-180 | 1.95 |
| MY SM 10143 | >250 |
| NE CA 8193 | 31.3 |
| PS AE 10145 | >250 |
| ES CO 9637 | 7.81 |
| ES IN 65-1 | >250 |
| SA PA 11737 | 3.90 |
| EN AE 13048 | >250 |
| KL PN 10031 | 3.90 |
| BO BR 4617 | 7.81 |
| PR VU 6896 | 15.6 |
| HE SP 9955 | >250 |
| ES CO 920 | 15.6 |

EXAMPLE 3

A second preparation of 7-[2-(4,5-dihydro-5-imino-1,3,4-thiadiazol-2-ylthio)acetamido]cephalosporanic acid prepared as described in Example 1 is tested as described in Example 2. The minimum inhibitory concentrations obtained are as follows:

| Organism | MIC (μg/ml.) |
|---|---|
| BA SU 6633 | .122 |
| ST AU 6538P | .976 |
| ST AU SMITH | .488 |
| ST AU CHP | 1.95 |
| ST AU 3-180 | 3.90 |
| MY SM 10143 | >250 |
| NE CA 8193 | 62.5 |
| PS AE 10145 | >250 |
| ES IN 65-1 | >250 |
| SA PA 11737 | 3.90 |
| EN AE 13048 | >250 |
| ES CO 9637 | 31.3 |
| KL PN 10031 | 3.90 |
| BO BR 4617 | 3.90 |
| PR VU 6896 | 3.90 |
| HE SP 9955 | >250 |
| ES CO 920 | 3.90 |

EXAMPLE 4

Following the procedure of Example 2 but substituting the organisms listed below the same preparation of 7-[2-(4,5-dihydro-5-imino-1,3,4-thiadiazol-2-ylthio)acetamido]cephalosporanic acid (Compound A) as used in Example 3, a third sample of the same compound, prepared as described in Example 1 (Compound B) and 7-[2-(5-acetamido-1,3,4-thiadiazol-2-ylthio)acetamido]cephalosporanic acid (Compound C) are tested to obtain the results shown:

| Organism | MIC (μg/ml.) Compound | | |
|---|---|---|---|
|  | A | B | C |
| Shigella flexneri 12025 | 31.3 | 7.81 | 15.6 |
| Shigella boydii 9207 | 62.5 | 62.5 | 31.3 |
| Shigella sonnei 11060 | 62.5 | 62.5 | 62.5 |
| Edwardsiella tarda 15947 | 31.3 | 15.6 | 7.81 |
| Salmonella cholera-suis 13312 | 1.95 | 1.95 | 15.6 |
| Salmonella typhi 19430 | 1.95 | 1.95 | 15.6 |
| Salmonella enteritidis 13076 | 1.95 | 1.95 | 31.3 |
| Arizona arizonae 13314 | 3.90 | 1.95 | 31.3 |
| Citrobacter freundii 8090 | >250 | >250 | >250 |
| Citrobacter diversus 27156 | 1.95 | 1.95 | 15.6 |
| Klebsiella pneumoniae 13883 | 15.6 | 7.81 | 62.5 |
| Klebsiella ozaenae 11296 | 1.95 | 1.95 | 7.81 |
| Klebsiella rhinoscleromatis 13884 | >250 | >250 | >250 |
| Enterobacter cloacae 13047 | >250 | >250 | >250 |
| Enterobacter havniae 11604 | >250 | >250 | 250 |
| Enterobacter agglomerans 27155 | 15.6 | 7.81 | 7.81 |
| Serratia marcescens 13880 | >250 | >250 | >250 |
| Serratia liquefaciens 27592 | >250 | >250 | >250 |
| Serratia rubidae 27593 | >250 | >250 | >250 |
| Providencia alcalifaciens 9886 | >250 | >250 | >250 |
| Providencia stuartii 25825 | 250 | 250 | 250 |
| Proteus mirabilis 9921 | 7.81 | 7.81 | 15.6 |
| Proteus rettgeri 9918 | NA | 250 | NA |
| Acinetobacter calcoaceticus 9957 | 7.81 | 7.81 | 250 |

EXAMPLE 5

Mice are infected intraperitoneally with a standardized suspension of Staphylococcus aureaus CHP in 5% gastric mucin. The animals are randomized. Six hours post-infection a single dose of the compound indicated is administered by the route indicated. The animals are observed for a 30 day period and deaths are recorded daily. The $CD_{50}$ for 14 and 30 days as determined by the method of Reed and Muench, American Journal of Hygiene (1938), for each compound is tabulated:

| Compound | Route of Administration | Dose (mg/kg.) | Deaths Total No. Treated | | $CD_{50}$ | |
|---|---|---|---|---|---|---|
| | | | 14 Days | 30 Days | 14 Days | 30 Days |
| Nafcillin | Subcutaneous | 400 | 3/10 | 4/10 | 3.12 | 3.90 |
| | | 200 | 3/10 | 4/10 | | |
| | | 100 | 9/10 | 10/10 | | |
| | | 50 | 9/10 | 9/10 | | |
| | | 400 | 4/10 | 4/10 | 3.41 | 3.41 |
| | | 200 | 4/10 | 4/10 | | |
| | | 100 | 7/10 | 7/10 | | |
| | | 50 | 10/10 | 10/10 | | |
| Cefazolin | Subcutaneous | 400 | 4/10 | 5/10 | 6.41 | 7.2 |
| | | 200 | 10/10 | 10/10 | | |
| | | 100 | 10/10 | 10/10 | | |
| | | 50 | 10/10 | 10/10 | | |
| | | 400 | 4/10 | 5/10 | 5.82 | 7.2 |
| | | 200 | 10/10 | 10/10 | | |
| | | 100 | 8/10 | 10/10 | | |
| | | 50 | 10/10 | 10/10 | | |
| Untreated Controls | | | | 31/33 | | |
| 7-[2-(4,5-dihydro-5-imino-1,3,4-thiadiazol-2-ylthio)acetamido]cephalosporanic acid | Oral | 800 | 0/10 | 1/10 | 3.21 | 3.40 |
| | | 400 | 0/10 | 0/10 | | |
| | | 200 | 4/10 | 4/10 | | |
| | | 100 | 10/10 | 10/10 | | |

EXAMPLE 6

7-[2-(5-Acetylamino-1,3,4-thiadiazol-2-ylthio)acetamido]cephalosporanic acid is tested as described in Example 5. This compound exhibits a $CD_{50}$ of greater than 7.2 mg. per kg. when administered orally. This indicates a lack of significant oral activity against the test organism employed.

The subject matter which the applicant regards as his invention is particularly pointed out and distinctly claimed as follows:

1. A chemical compound having the formula:

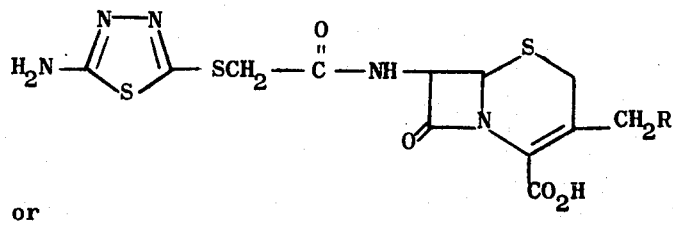

or

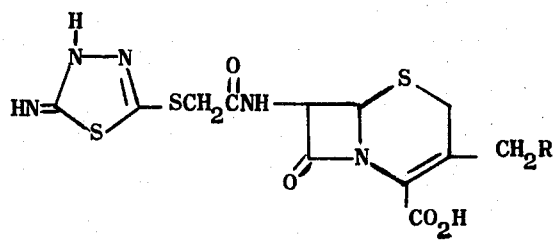

wherein

R is hydrogen or acetoxy and the pharmaceutically acceptable addition salts thereof.

2. A compound as defined in claim 1 which is 7-[2-(4,5-dihydro-5-imino-1,3,4-thiadiazol-2-ylthio)acetamido]cephalosporanic acid.

3. A compound as defined in claim 1 which is 7-[2-(4,5-dihydro-5-imino-1,3,4-thiadiazol-2-ylthio)acetamido]cephalosporanic acid, hydrobromide.

* * * * *